United States Patent [19]

Iyengar et al.

[11] Patent Number: 6,150,396
[45] Date of Patent: *Nov. 21, 2000

[54] METHODS OF TREATING OR PREVENTING INTERSTITIAL CYSTITIS

[75] Inventors: Smriti Iyengar, Carmel; Mark A. Muhlhauser, Indianapolis, both of Ind.; Karl B. Thor, Morrisville, N.C.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/142,780

[22] PCT Filed: Mar. 7, 1997

[86] PCT No.: PCT/US97/03410

§ 371 Date: Sep. 8, 1998

§ 102(e) Date: Sep. 8, 1998

[87] PCT Pub. No.: WO97/33880

PCT Pub. Date: Sep. 18, 1997

[51] Int. Cl.[7] .................................................. A61K 31/381
[52] U.S. Cl. ................................................................ 514/438
[58] Field of Search ............................................. 514/438

[56] References Cited

U.S. PATENT DOCUMENTS 5,744,474   4/1998   Thor ....................................... 514/357

OTHER PUBLICATIONS

Thor et al., J. Pharmacology & therapeutics, 274(2), 1014–24, Aug. 1995.

*Primary Examiner*—Phyllis G. Spivack
*Attorney, Agent, or Firm*—Suzanne M. Harvey; Paul J. Gaylo; Arvie J. Anderson

[57] ABSTRACT

This invention provides methods for the treatment or prevention of interstitial cystitis or urethral syndrome in a mammal which comprise administering to a mammal in need thereof an effective amount of duloxetine.

3 Claims, No Drawings

METHODS OF TREATING OR PREVENTING INTERSTITIAL CYSTITIS

This case is a 371 of PCT/USA97/03410 filed Mar. 7, 1997.

BACKGROUND OF THE INVENTION

Interstitial cystitis is a chronic debilitating inflammatory disorder of the bladder. The disease is most common in women ranging in age from about thirty to sixty with onset of the condition typically occurring at about forty years of age. It is characterized by a number of urinary difficulties, such as suprapubic pressure and pain, with bladder filling, urinary frequency, nocturia, dysuria, urgency adn irritative voiding associated with morphological and histological changes in the bladder. The condition is characterized as "interstitial cystitis" because it is believed the condition does not affect the surface of the bladder, but instead involves the spaces between the cells, namely the interstices, in the lining of the bladder.

Urethral syndrome is a related painful voiding disorder of unknown etiology affecting women exhibiting many of the conditions set forth above.

As noted in U.S. Pat. No. 5,145,859, issued Sep. 8, 1992, the entire contents of which are herein incorporated by reference, there are a number of compounds proposed to treat these conditions, based on differing theories as to the etiology of interstitial cystitis and urethral syndrome. None of these treatment regimens has proven completely successful to date.

Because of the current dissatisfaction of the currently marketed treatments for interstitial cystitis within the affected population, there exists a need for a more efficacious and safe treatment.

SUMMARY OF THE INVENTION

This invention provides methods for the treatment or prevention of interstitial cystitis or urethral syndrome in a mammal which comprise administering to a mammal in need thereof an effective amount of duloxetine.

DETAILED DESCRIPTION AND PREFERRED EMBODIMENTS

Duloxetine is N-methyl-3-(1-naphthalenyloxy)-3-(2-thienyl)propanamine. It is usually administered as the (+) enantiomer, and as the hydrochloride salt. It was first taught by U.S. Pat. No. 4,956,388, which teaches the synthesis of the compound as well as its high potency as an uptake inhibitor of both serotonin and norepinephrine. The word "duloxetine" will be used here to refer to any acid addition salt or the free base of the molecule, as well as to either an enantiomer or the racemate. It is to be understood, however, that the (+) enantiomer is preferred.

The term "treating" (or "treat") as used herein includes its generally accepted meaning which encompasses prohibiting, preventing, restraining, and slowing, stopping, or reversing progression, severity, or a resultant symptom. As such, the methods of this invention encompass both therapeutic and prophylactic administration.

Duloxetine is a safe drug, and its use in treating or preventing interstitial cystitis or urethral syndrome, in both adults and children, is a superior treatment for that disorder because of its improved safety. The compound is particularly selective, having few if any physiological effects besides those on norepinephrine and serotonin processing, and therefore is free of side effects and unwanted activities. Further, it is effective at relatively low doses, as discussed below, and may safely and effectively be administered once per day. Thus, difficulties created by the multiple dosing of patients, who are children and disorganized adults, are completely avoided.

The most preferred dose of duloxetine for the treatment of a given patient with any particular disorder will vary, depending on the characteristics of the patient, as all clinicians and medical doctors are aware. Factors such as other diseases from which the patient suffers, the patient's age and size, and other medications which the patient may be using will have an effect on the duloxetine dose and will be taken into account. In general, however, the daily dose of duloxetine is from about 1 to about 80 mg. A more preferred dose range is from about 5 to about 40 mg, and another preferred range is from about 5 to about 20 mg, administered once daily.

Duloxetine is orally available and presently is orally administered, in the form of a tablet or a capsule full of enteric coated granules. Oral administration in such forms is preferred in the practice of the present invention. However, other routes of administration are also practical and may be preferred in certain cases. For example, transdermal administration may be very desirable for patients who are forgetful or petulant about taking oral medicine. Sustained release formulations, oral or percutaneous, may be prepared, but are not preferred because duloxetine is quite effective when administered once daily and there is little benefit from the additional effort of preparing the sustained action product.

In general, the formulation of duloxetine for use in the present invention follows the methods used in formulating duloxetine for other purposes, and indeed methods usual in pharmaceutical science are appropriate. However, a preferred formulation of duloxetine comprises enteric pellets, or granules, of which a number are charged in a gelatin capsule.

The preferred duloxetine enteric formulation comprises a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer. The following example demonstrates the preparation of a preferred such formulation.

EXAMPLE

10 mg Duloxetine Base/Capsule

| Bill of Materials | |
|---|---|
| Beads | |
| Sucrose - starch nonpareils, 20–25 mesh | 60.28 mg |
| Duloxetine layer | |
| Duloxetine | 11.21 |
| Hydroxypropylmethylcellulose | 3.74 |
| Separating layer | |
| Hydroxypropylmethylcellulose | 2.51 |
| Sucrose | 5.00 |
| Talc, 500 mesh | 10.03 |
| Enteric layer | |
| HPMCAS, LF grade, Shin-Etsu Chemical | 25.05 |

-continued

| Bill of Materials | |
|---|---|
| Co., Tokyo, Japan | |
| Triethyl citrate | 5.00 |
| Talc, 500 mesh | 7.52 |
| Finishing layer | |
| Hydroxypropylmethylcellulose | 8.44 |
| Titanium dioxide | 2.81 |
| Talc | Trace |
| | 141.60 mg |

The duloxetine layer was built up by suspending duloxetine in a 4% w/w solution of the hydroxypropylmethylcellulose in water, and milling the suspension with a CoBall Mill (Fryma Mashinen AG, Rheinfelden, Switzerland) model MS-12. A fluid bed dryer with a Wurster column was used to make this product, at a batch size of 1.0 kg. The separating layer was added from a 4% w/w solution of the hydroxypropylmethylcellulose in water, in which the sucrose was also dissolved.

In order to prepare the enteric coating suspension, purified water was cooled to 10° C. and the polysorbate, triethyl citrate and silicone emulsion were added and dispersed or dissolved. Then the HPMCAS and talc were added and agitated until homogeneity was obtained, and the HPMCAS was fully neutralized by addition of ammonium hydroxide until solution of the polymer was complete. To this suspension, a carboxymethylcellulose aqueous solution, 0.5% w/w, was added and blended thoroughly. The enteric suspension was maintained at 20° C. during the coating process. The enteric suspension was then added to the partially completed pellets in the Wurster column at a spray rate of about 15 ml/min, holding the temperature of the inlet air at about 50° C. The product was dried in the Wurster at 50° C. when the enteric suspension had been fully added, and then dried on trays for 3 hours in a dry house at 60° C. A finishing layer was then applied which consisted of a 4.5% w/w/hydroxypropylmethyl-cellulose solution containing titanium dioxide and propylene glycol as plasticizer. The pellets were completely dried in the fluid bed dryer and then were then filled in size 3 gelatin capsules.

The patient to be benefited by practice of the present invention is a patient having one or more of the disorders discussed in detail below, or who is at a heightened risk of contracting such disorder. Diagnosis of these disorders, or the identification of a patient at risk of one or more of them, is to be made by a physician or psychiatrist. It is presently believed that duloxetine's potency in inhibiting the uptake of serotonin and norepinephrine is the mechanism by which it benefits such patients, by alleviating the effects of the disorder from which the patient suffers, or even eliminating the disorder completely.

It has been determined that the method of the present invention is effective in treating mammals, particularly middle-aged women, exhibiting symptoms of interstitial cystitis and/or urethral syndrome. In this regard, the clinical and local immune response to the compounds of the present invention is investigated in an open trail with 10 female interstitial cystitis patients, whose disease is diagnosed according to the consensus criteria developed in 1987 at a National Institutes of Health workshop. To make objective the symptoms and the clinical response of the patients the present inventors scored (scale 0 to 2) the symptoms of frequency, urgency, nocturia, dysuria and suprapubic pain, as described in U.S. Pat. No. 5,145,859, issued Sep. 8, 1992, the entire contents of which are herein incorporated by reference. A compound of the present invention is administered as a single daily dose determined by a dose-titration test. Urinary interleukin-2 inhibitory activity (IL-2-IN), a marker of cell-mediated inflammation, is measured using a murine interleukin-2 dependent cell line.

The patients are reviewed for reduction in clinical symptoms. Drug side-effects are minimal. Urinary IL-2-IN activity before therapy confirms the presence of cell-mediated inflammation: after 4 months of therapy IL-2-IN activity is normal in most of the patients, regardless of the severity of symptoms, which indicates that the compounds of Formula I exerts an immunosuppressive effect. The data suggests that the compounds of Formula I can be an efficacious, well-tolerated, convenient oral medication for the treatment of interstitial cystitis.

In addition, as more clearly demonstrated below in Example 2, the present inventors also observes similar responses in regard to the treatment of urethral syndrome. As a result, the test data clearly indicates that the compounds employed in the present invention can be effective therapeutic agents for the treatment of interstitial cystitis and/or urethral syndrome.

As a result, it has been found that duloxetine is particularly well-suited for the treatment of interstitial cystitis and/or urethral syndrome because they not only provide effective relief, are available for oral administration, and are relatively inexpensive. It has been discovered that patients receiving duloxetine substantially reduce the pathological conditions exhibited by these two painful bladder disorders, and are able to carry on their daily activities in a relatively normal existence in comparison with their pre-treatment state.

The present invention will be further described according to the following non-limiting examples.

Example 1

Materials and Methods

Patients:

The diagnosis of interstitial cystitis is assigned to 10 female patients, aged 23 to 51 years, in accordance with the consensus criteria established at the National Institutes of Health workshop on interstitial cystitis, August, 1987 (Gillenwater, J. Y. and Wein, A. J.: Summary of the National Institute of Arthritis, Diabetes, Digestive and Kidney Diseases Workshop on Interstitial Cystitis, National Institutes of Health, Bethesda, Md., Aug. 28–29, 1987, J. Urol., 140:203, 1988), and U.S. Pat. No. 5,145,859:

| Interstitial Cystitis: Criteria for Diagnosis | |
|---|---|
| Inclusion Criteria | Exclusion Criteria |
| Hunner's Ulcer (if present, automatic inclusion) | less than 18 years old<br>benign or malignant tumors<br>radiation, tuberculous,<br>bacterial |
| Positive Factors (at least 2 required for inclusion): | or cyclophosphamide cystitis<br>vaginitis<br>duration of symptoms <1 year |
| suprapubic, pelvic, urethral, vaginal or perineal pain | gynecologic cancer<br>urethral diverticulum, bladder<br>or lower ureteral calculi |

-continued

Interstitial Cystitis: Criteria for Diagnosis

| Inclusion Criteria | Exclusion Criteria |
|---|---|
| glomerulations at cystoscopy after bladder distension (80 cm water pressure × 1 min.) | active herpes (HSV II) waking frequency <5 in 12 hrs. nocturia <2 neurogenic bladder dysfunction |
| decreased compliance on cystometrogram | waking capacity >400 ml, absence of urgency with bladder filling symptoms relieved by antibiotics, urinary |
| pain on bladder filling relieved by emptying | urinary analgesics or antiseptics |

Cystometrics are performed after cessation of other modes of therapy and prior to institution of therapy: all patients had a waking bladder capacity of less than 350 ml (range 150 ml to 340 ml).

Symptom Evaluation:

The symptom scores (total score range: 0 to 10) form the basis for the evaluation of treatment efficacy. The severity of each symptom is assigned a numerical value, as follows:

Symptom Severity Survey

| Symptom | Description | Score |
|---|---|---|
| Frequency (daytime) | voids once every 3 to 5 hours | 0 |
| | voids once every 1 to 2 hours | 1 |
| | voids more than once every hour | 2 |
| Urgency | urge to void equal to actual frequency | 0 |
| | urge to void exceeds actual frequency | 1 |
| | constant urge to void | 2 |
| Nocturia | no nocturia, or 1 void nightly | 0 |
| | nocturia 2 to 4 times nightly | 1 |
| | more than 4 times nightly | 2 |
| Dysuria | no dysuria | 0 |
| | intermittent dysuria | 1 |
| | dysuria with each void | 2 |
| Suprapubic pain (abdomino-perineal) | no pain | 0 |
| | intermittent pain | 1 |
| | constant pain | 2 |

At the time of diagnosis, and before any treatment, any patient who falls within the parameters of the inclusion of exclusion descriptors of the NIH workshop consensus criteria (above) will score at least a "4" on this survey (frequency<1; urgency<1; nocturia<1; and either dysuria or suprapubic pain<1).

Urine Collection:

Urine specimens are collected from all patients before and during therapy. Voided urine is centrifuged at 1000×g for 10 minutes at 4° C. and the supernatant separated from the sediment. The urine supernatant is subjected to $0.2\mu$ filtration (celluloseacetate) at 4° C. to remove any bacteria and debris, and a 1 ml aliquot is removed for creatinine measurement (CREATININE II ANALYZER™, Beckman Instruments, Inc., Brea, Calif.). The supernatant is ultrafiltered against 3×volume in phosphate-buffered saline PBS) with 0.1 $\mu$g/ml albumin (Sigma, St. Louis, Mo.) using a filtration device (5,000 MW cut off; Amicon, Deavers, Mass.). The concentrated supernatant is dialyzed using 3,500 MW cutoff tubing, shell frozen with dry ice, and vacuum lyophilized. The powder is stored at −20° C.

Measurement of IL-2-IN Activity: The bioassay for IL-2-IN is modified from the method for measuring IL-2 activity described by Gillis and associates. S. Gillis, et al., "T-Cell Growth Factor: Parameters Of Production And A Quantitative Microassay For Activity, *Journal of Immunology*, 120:2027, (1978). The murine IL-2-dependent cytotoxic T-cell line (CTLL-N) is derived from the CT-6 cell line. J. Kusugami, et al., "Intestinal Immune Reactivity To Interleukin-2 Differs Among Crohn's Disease, Ulcerative Colitis And Controls", *Gastroenterology*, 97:1 (1989). The CTLL-Ns are maintained in liquid culture using a 1:1 mixture of Roswell Park Memorial Institute (RPMI 1640 and Dulbecco's Modified Eagles Medium (DMEM; 4.5 g/L glucose) media supplemented with 2.9 mg/ml glucose, 9.4 mM HEPES buffer, 1.9 mg/ml glutamine, 289 $\mu$g/ml arginine, 0.12 M non-essential amino acids, $5\times10^{-5}$ M 2-mercaptoethanol, 4.5% fetal bovine serum, 90 units/ml penicillin, 90 $\mu$g/ml streptomycin, 22 $\mu$g/ml fungizone, 0.45 mg/ml gentamicin and 20 units/ml of human recombinant IL-2.

The CTLL-Ns are washed and suspended at a concentration of $10^{-5}$/ml in the culture media. Assays are performed in triplicate, as follows: a serial dilution of the sample aliquot (50 $\mu$l), a 1:10 dilution of the human recombinant IL-2 standard and $10^{-4}$ CTLL-Ns (100 $\mu$l) are placed in microliter wells. The microliter plates are incubated in a humidified 6% $CO_2$ atmosphere at 37° C. for 24 hrs, and the cells are pulsed at the 19th hour with 1 $\mu$Ci/well of methyl-tritiated thymidine (specific activity 6.7 Ci/mM, New England Nuclear, I. E. Dupont, Boston, Mass.).

The cells are collected onto glass filter paper discs. The discs are placed in scintillation fluid and thymidine uptake is measured by liquid scintillation spectrophotometry. IL-2 inhibitory activity is calculated by modified probit analysis.

The proliferation "maximum" is the tritiated thymidine uptake caused by the amount of exogenous IL-2 activity in the control microliter wells, assessed in quadruplicate for each assay. The proliferation "minimum" is derived from lowest amount of tritiated thymidine uptake caused by the IL-2 inhibitor standard. The probit calculation corrected for minor interassay variations of thymidine uptake in control wells, and permitted interassay comparisons of inhibitor activity among the urine samples. By this treatment of the data, the calculated value of IL-2 inhibitory activity in lyophilized urine samples varies less than 10% from assay to assay. IL-2-IN activity is expressed in units/mg urine creatinine (U/mg u.c.). IL-2-IN activity is less than 0.05 U/mg u.c. in the urine of healthy adults. J. Fleischmann, et al., *Journal of Biological Regulators and Homeostatic Agents*, 4:73, (1990).

Medication Assignments:

All patients are treated initially with a total daily dose of 30 mg, which is administered as a single, extended release tablet.

Patient Monitoring:

Patients are interviewed and blood pressure measured twice monthly during the first 2 months of therapy, during the first 2 months after a dose escalation, and then once monthly thereafter. The symptom severity score at each interview is based on the patient's experiences during the previous 24 hours.

Example 2

In addition to the treatment of patients with interstitial cystitis, patients with the urethral syndrome have been treated with duloxetine, using the titration test and treatment protocol described in U.S. Pat. No. 5,145,859. Similar to the data of Example 1, the positive response to the compounds of the present invention in this limited study supports the hypothesis that the urethral syndrome and interstitial cystitis are both part of the same disease spectrum, perhaps as variants of reflex sympathetic dystrophy.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See. e.g, REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day. In addition to the enteric tablet formulation described, supra, the present invention also employs methods of treating or preventing interstitial cystitis or urethral syndrome employing duloxetine in a number of formulations. Examples of such formulations follow.

Formulation Preparation 1
Hard gelatin capsules containing the following ingredients are prepared:

| Ingredient | Quantity (mg/capsule) |
| --- | --- |
| Active Ingredient(s) | 30.0 |
| Starch | 305.0 |
| Magnesium stearate | 5.0 |

The above ingredients are mixed and filled into hard gelatin capsules in 340 mg quantities.

Formulation Preparation 2
A tablet formula is prepared using the ingredients below

| Ingredient | Quantity (mg/tablet) |
| --- | --- |
| Active Ingredient(s) | 25.0 |
| Cellulose, microcrystalline | 200.0 |
| Colloidal silicon dioxide | 10.0 |
| Stearic acid 5.0 | |

The components are blended and compressed to form tablets, each weighing 240 mg.

Formulation Preparation 3
A dry powder inhaler formulation is prepared containing the following components

| Ingredient | Weight % |
| --- | --- |
| Active Ingredient(s) | 5 |
| Lactose | 95 |

The active mixture is mixed with the lactose and the mixture is added to a dry powder inhaling appliance.

Formulation Preparation 4
Tablets, each containing 30 mg of active ingredient, are prepared as follows

| Ingredient | Quantity (mg/tablet) |
| --- | --- |
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5
Capsules, each containing 40 mg of medicament are made as follows

| Ingredient | Quantity (mg/capsule) |
| --- | --- |
| Active Ingredient(s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6
Suppositories, each containing 25 mg of active ingredient are made as follows

| Ingredient | Amount |
| --- | --- |
| Active Ingredient(s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool Formulation Preparation 7
Suspensions, each containing 50 mg of medicament per 5.0 ml dose are made as follows

| Ingredient | Amount |
| --- | --- |
| Active Ingredient(s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8
Capsules, each containing 15 mg of medicament, are made as follows

| Ingredient | Quantity (mg/capsule) |
| --- | --- |
| Active Ingredient(s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9
An intravenous formulation may be prepared as follows

| Ingredient | Quantity |
| --- | --- |
| Active Ingredient(s) | 250.0 mg |
| Isotonic saline | 1000 ml |

Formulation Preparation 10
A topical formulation may be prepared as follows

| Ingredient | Quantity |
| --- | --- |
| Active Ingredient(s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11
Sublingual or buccal tablets, each containing 10 mg of active ingredient, may be prepared as follows

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous string and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g, U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drag to render the drug more lipid soluble and amenable to transportation across the blood-brain barer. Alternatively, the delivery of hydrophilic drugs may be enhanced by intra-arterial infusion of hypertonic solutions which can transiently open the blood-brain barrier.

We claim:

1. A method for the treatment or prevention of interstitial cystitis or urethral syndrome in a mammal which comprise administering to a mammal in need thereof an effective amount of duloxetine.

2. A method as claimed in claim 1 wherein the mammal is administered between 30 and 150 mg of duloxetine per day.

3. A method as claimed in claim 2 wherein the duloxetine is administered as an enteric tablet.

* * * * *